United States Patent [19]

Matsuo et al.

[11] Patent Number: 4,935,432
[45] Date of Patent: Jun. 19, 1990

[54] INDOLYLPIPERIDINE COMPOUNDS, PROCESSES FOR THE PREPARATION THEREOF AND PHARMACEUTICAL COMPOSITION COMPRISING THE SAME

[75] Inventors: Masaaki Matsuo; Takashi Manabe, both of Osaka; Shinji Shigenaga, Kobe; Hiroshi Matsuda, Osaka, all of Japan

[73] Assignee: Fujisawa Pharmaceutical Co., Ltd., Osaka, Japan

[21] Appl. No.: 295,569

[22] Filed: Jan. 11, 1989

[30] Foreign Application Priority Data

Jan. 14, 1988 [GB] United Kingdom ................ 8800795
Aug. 1, 1988 [GB] United Kingdom ................ 8818260

[51] Int. Cl.$^5$ .................. C07C 103/22; C07C 103/26
[52] U.S. Cl. ..................................... 514/323; 546/201
[58] Field of Search .......................... 514/323; 546/201

[56] References Cited

U.S. PATENT DOCUMENTS

| | | | |
|---|---|---|---|
| 3,850,938 | 11/1974 | Derible et al. ...................... | 546/201 |
| 3,950,527 | 4/1976 | Derible et al. ...................... | 546/201 X |
| 3,993,764 | 11/1976 | Dumont et al. ...................... | 424/267 |
| 4,100,291 | 7/1978 | Clemence et al. ................... | 514/321 |
| 4,359,468 | 11/1982 | Freter et al. ....................... | 424/267 |
| 4,443,461 | 4/1984 | Ward ................................. | 546/201 X |
| 4,530,932 | 7/1985 | Clemence et al. ................... | 514/318 |
| 4,548,939 | 10/1985 | Kennis et al. ....................... | 514/265 |
| 4,581,355 | 4/1986 | Tahara et al. ...................... | 546/201 X |
| 4,742,057 | 5/1988 | Ueda et al. ........................ | 514/235.42 |

FOREIGN PATENT DOCUMENTS

| | | |
|---|---|---|
| 0157420 | 10/1985 | European Pat. Off. . |
| 02003322 | 11/1986 | European Pat. Off. . |
| 57-188567 | 11/1982 | Japan ..................... 546/201 |
| 1425354 | 2/1976 | United Kingdom ................ 546/201 |
| 2093455 | 9/1982 | United Kingdom . |

OTHER PUBLICATIONS

Archibald et al., "Benzamidopiperidines. 3 . . . ", J. Med. Chem., 1974, vol. 17, No. 7, 739-44.

D. Beck & K. Schenker, Synthese von 2- und 3-(1,2,3-,6-Tetrahydrdopyridyl)-indolen, Helv. Chim. Acta, 51, 260-264, (1968).

*Primary Examiner*—Mary C. Lee
*Assistant Examiner*—Catherine S. Kilby Scalzo
*Attorney, Agent, or Firm*—Oblon, Spivak, McClelland, Maier & Neustadt

[57] ABSTRACT

The invention relates to new compounds, of antiallergic activity, of the formula:

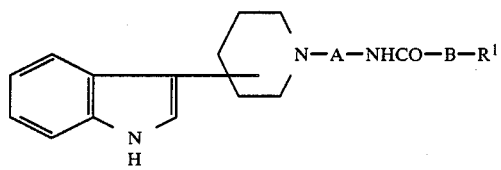

wherein $R^1$ is aryl substituted with substituent(s) selected from the group consisting of hydroxy, protected hydroxy, halogen and lower alkoxy, A is lower alkylene, and B is lower alkenylene, or a pharmaceutically acceptable salt thereof.

10 Claims, No Drawings

INDOLYLPIPERIDINE COMPOUNDS, PROCESSES FOR THE PREPARATION THEREOF AND PHARMACEUTICAL COMPOSITION COMPRISING THE SAME

This invention relates to new indolylpiperidine compounds and pharmaceutically acceptable salts thereof.

More particularly, it relates to new indolylpiperidine compounds and pharmaceutically acceptable salts thereof which have antiallergic activity, to processes for the preparation thereof, to a pharmaceutical composition comprising the same and to a method for the treatment of allergic disease in human being or animals.

One object of this invention is to provide new indolylpiperidine compounds and pharmaceutically acceptable salts thereof which possess antiallergic activity.

Another object of this invention is to provide processes for the preparation of said indolylpiperidine compounds or salts thereof.

A further object of this invention is to provide a pharmaceutical composition comprising, as an active ingredient, said indolylpiperidine compounds or pharmaceutically acceptable salts thereof.

Still further object of this invention is to provide a therapeutical method for the treatment of allergic disease such as allergic asthma, allergic rhinitis, allergic conjunctivitis, chronic urticaria, or the like, in human being or animals.

Some indolypiperidine compounds having anti-allergic activity have been known as described in British Patent Application Publication No. 2093455.

Some amide derivatives having anti-allergic activity have been known as described in European Patent Application Publication No. 157420.

The object indolylpiperidine compounds of this invention are new and can be represented by the following general formula [I]:

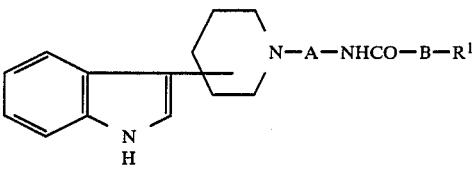

wherein
R[1] is aryl substituted with substituent(s) selected from the group consisting of hydroxy, protected hydroxy, halogen and lower alkoxy,
A is lower alkylene, and
B is lower alkenylene.

The object compound [I] or its salt can be prepared by processes as illustrated in the following reaction schemes.

PROCESS 1

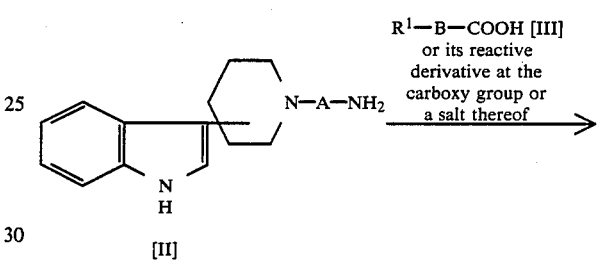

PROCESS 2

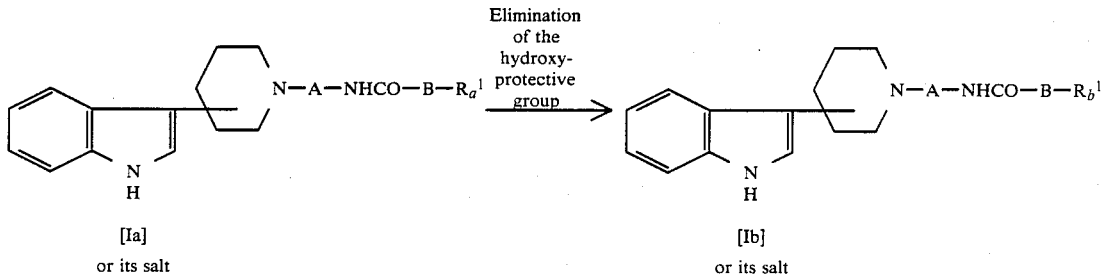

PROCESS 3

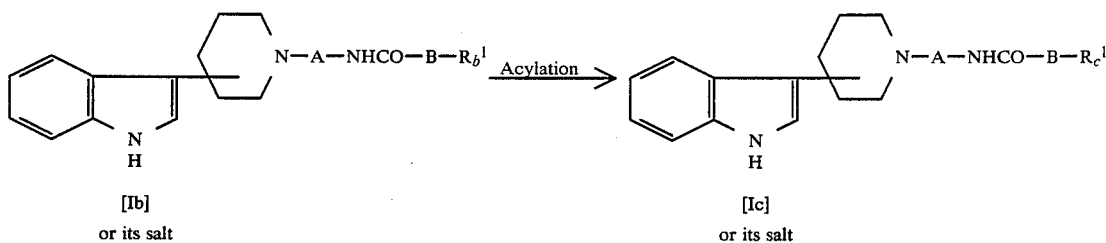

[Ib]
or its salt

[Ic]
or its salt wherein
$R_a^1$ is aryl substituted with protected hydroxy, with protected hydroxy and halogen, or with protected hydroxy and lower alkoxy, $R_b^1$ is aryl substituted with hydroxy, with hydroxy and halogen, or with hydroxy and lower alkoxy, $R_c^1$ is aryl substituted with acyloxy, with acyloxy and halogen, or with acyloxy and lower alkoxy, and $R^1$, A and B are each as defined above.

In the above and subsequent descriptions of the present specification, suitable examples of the various definitions to be included within the scope of the invention are explained in detail in the following.

The term "lower" is intended to mean a group having 1 to 6 carbon atom(s) unless otherwise provided.

Suitable "aryl" may be phenyl, naphthyl, phenyl substituted with lower alkyl [e.g. tolyl, mesityl, cumenyl, xylyl, diethylphenyl, diisopropylphenyl, di-tert-butyl-phenyl, etc.] or the like.

Suitable "protected hydroxy" may be substituted lower alkoxy such as lower alkoxy(lower)alkoxy(lower)alkoxy [e.g. methoxyethoxymethoxy, etc.], substituted or unsubstituted ar(lower)alkoxy [e.g. benzyloxy, nitrobenzyloxy, etc.], acyloxy such as lower alkanoyloxy [e.g. formyloxy, acetyloxy, propionyloxy, butyryloxy, isobutyryloxy, valeryloxy, isovaleryloxy, pivaloyloxy, hexanoyloxy, 3,3-dimethylbutyryloxy, etc.], lower alkoxycarbonyloxy [e.g. methoxycarbonyloxy, ethoxycarbonyloxy, propoxycarbonyloxy, isopropoxycarbonyloxy, butoxycarbonyloxy, isobutoxycarbonyloxy, tert-butoxycarbonyloxy, pentyloxycarbonyloxy, hexyloxycarbonyloxy, etc.], sulfonyloxy [e.g. mesyloxy, tosyloxy, benzenesulfonyloxy, etc.], substituted or unsubstituted ar(lower)alkoxycarbonyloxy [e.g. benzyloxycarbonyloxy, bromobenzyloxycarbonyloxy, etc.] etc., tri(lower)alkysilyloxy [e.g. trimethylsilyloxy, etc.] or the like.

Suitable "halogen" is fluorine, chlorine, bromine and iodine.

Suitable "acyloxy" may be the same as above-mentioned acyloxy enumerated for protected hydroxy.

Suitable "lower alkoxy" may be a straight or branched one such as methoxy, ethoxy, propoxy, isopropoxy, butoxy, isobutoxy, tert-butoxy, pentyloxy, hexyloxy or the like, in which the preferable one is $C_1$-$C_4$ alkoxy and the most preferable one is methoxy.

Preferable examples of "aryl substituted with substituent(s) selected from the group consisting of hydroxy, protected hydroxy, halogen and lower alkoxy" may be mono-, or di-, or trihydroxyphenyl; mono-, or di-, or tri(halo)phenyl [e.g. chlorophenyl, fluorophenyl, dichlorophenyl, trifluorophenyl, etc.]; mono-, or di-, or tri(lower)alkylphenyl [e.g. tolyl, mesityl, cumenyl, xylyl, ethylphenyl, diethylphenyl, isopropylphenyl, diisopropylphenyl, di-tert-butylphenyl, etc.]; mono-, or di-, or tri(lower)alkoxyphenyl [e.g. methoxyphenyl, ethoxyphenyl, dimethoxyphenyl, trimethoxyphenyl, diethoxyphenyl, diisopropoxyphenyl, etc.]; mono-, or dihydroxy and mono-, or di(lower)alkoxy substituted phenyl [e.g. methoxy(hydroxy)phenyl, ethoxy(hydroxy)phenyl, isopropoxy(hydroxy)phenyl, dimethoxy(hydroxy)phenyl, diethoxy(hydroxy)phenyl, diisopropoxy(hydroxy)phenyl, methoxy(dihydroxy)phenyl, methoxy(ethoxy)hydroxyphenyl, etc.]; mono-, or dihydroxy and mono-, or di(lower)alkyl substituted phenyl [e.g. methyl(hydroxy)phenyl, ethyl(hydroxy)phenyl, propyl(hydroxy)phenyl, isopropyl(hydroxy)phenyl, dimethyl(hydroxy)phenyl, diethyl(hydroxy)phenyl, diisopropyl(hydroxy)phenyl, di-tert-butyl(hydroxy)phenyl, methyl(dihydroxy)phenyl, methyl(ethyl)hydroxyphenyl, etc.]; mono-, or dihydroxy and mono-, or dihalo substituted phenyl [e.g. chloro(hydroxy)phenyl, dichloro(hydroxy)phenyl, fluoro(hydroxy)phenyl, chloro(dihydroxy)phenyl, etc.]; mono-, or di-, or tri-protected hydroxy substituted phenyl such as mono-, or di-, or tri[lower alkoxy(lower)alkoxy(lower)alkoxy]phenyl [e.g. mono-, or di-, or tri(methoxyethoxymethoxy)phenyl, etc.], mono-, or di-, or triacyloxyphenyl [e.g. mono-, or di-, or tri(lower)alkanoyloxyphenyl (e.g. formyloxyphenyl, acetyloxyphenyl, propionyloxyphenyl, diacetyloxyphenyl, dipropionyloxyphenyl, triacetyloxyphenyl, etc.), mono-, or di-, or tri(lower)alkoxycarbonyloxyphenyl (e.g. methoxycarbonyloxyphenyl, ethoxycarbonyloxyphenyl, diethoxycarbonyloxyphenyl, triethoxycarbonyloxyphenyl, etc.), etc.] or the like; mono-, or di(lower)alkoxy and mono-, or di-protected hydroxy substituted phenyl such as mono-, or di(lower)alkoxy and mono-, or di[lower alkoxy(lower)alkoxy(lower)alkoxy]substituted phenyl [e.g. methoxy(methoxyethoxymethoxy)phenyl, ethoxy(methoxyethoxymethoxy)phenyl, dimethoxy(methoxyethoxymethoxy)phenyl, diethoxy(methoxyethoxymethoxy)phenyl, diisopropoxy(methoxyethoxymethoxy)phenyl, etc.], mono-, or diacyloxy and mono-, or di(lower)alkoxy substituted phenyl [e.g. mono-, or di(lower)alkanoyloxy and mono-, or di(lower)alkoxy substituted phenyl (e.g. acetyloxy(methoxy)phenyl, propionyloxy(methoxy)phenyl, acetyloxy(ethoxy)phenyl, acetyloxy(dimethoxy)phenyl, propionyloxy(dimethoxy)phenyl, acetyloxy(diethoxy)phenyl, acetyloxy(diisopropoxy)phenyl, diacetyloxy(methoxy)phenyl, etc.), mono-, or di(lower)alkoxycarbonyloxy and mono-, or di(lower)alkoxy substituted phenyl (e.g. methoxycarbonyloxy(methoxy)phenyl, ethoxycarbonyloxy(methoxy)phenyl, ethoxycarbonyloxy(ethoxy)phenyl, methoxycarbonyloxy(dimethoxy)phenyl, ethoxycarbonyloxy(dimethoxy)phenyl, ethoxycarbonyloxy(diethoxy)phenyl, ethoxycarbonyloxy(diisopropoxy)phenyl, etc.), etc.] or the like; mono-, or di(lower)alkyl and mono-, or di-protected hydroxy substituted phenyl such as mono-, or di(lower)alkyl and mono-, or di[lower alkoxy(lower)alkoxy(lower)alkoxy] substituted phenyl [e.g. methyl(methoxyethoxymethoxy)phenyl, ethyl(methoxyethoxymethoxy)phenyl, dimethyl(methoxyethoxymethoxy)phenyl, diethyl(methoxyethoxymethoxy)phenyl, diisopropyl(methoxyethoxymethoxy)phenyl, di-tert-butyl(methoxyethoxymethoxy)phenyl, etc.], mono-, or diacyloxy and mono-, or di(lower)alkyl substituted phenyl [e.g. mono-, or di(lower)alkanoyloxy and mono-, or di(lower)alkyl substituted phenyl (e.g. acetyloxy(methyl)phenyl, propionyloxy(methyl)phenyl, acetyloxy(ethyl)phenyl, acetyloxy(dimethyl)phenyl, propionyloxy(dimethyl)phenyl, acetyloxy(diethyl)phenyl, acetyloxy(diisopropyl)phenyl, diacetyloxy(methyl)phenyl, etc.), mono-, or di(lower)alkoxycarbonyloxy and mono-, or di(lower)alkyl substituted phenyl (e.g. methoxycarbonyloxy(methyl)phenyl, ethoxycarbonyloxy(methyl)phenyl, ethoxycarbonyloxy(ethyl)phenyl, methoxycarbonyloxy(dimethyl)phenyl, ethoxycarbonyloxy(dimethyl)phenyl, ethoxycarbonyloxy(diethyl)phenyl, ethoxycarbonyloxy(diisopropyl)phenyl, etc.), etc.] or the like; and mono-, or dihalo and mono-, or di-protected hydroxy substituted phenyl such as mono-, or dihalo and mono-, or di[lower alkoxy(lower)alkoxy(lower)alkoxy]substituted phenyl [e.g. chloro(methoxyethoxymethoxy)phenyl, dichloro(methoxyethoxymethoxy)phenyl, fluoro(methoxyethoxymethoxy)phenyl, etc.], mono-, or diacyloxy and mono-, or dihalo substituted phenyl [e.g. mono-, or di(lower)alkanoyloxy and mono-, or dihalo substituted phenyl (e.g. acetyloxy(chloro)phenyl, propionyloxy(chloro)phenyl, acetyloxy(dichloro)phenyl, etc.), mono-, or di(lower)alkoxycarbonyloxy and mono-, or dihalo substituted phenyl (e.g. methoxycarbonyloxy(chloro)phenyl, ethoxycarbonyloxy(chloro)phenyl, ethoxycarbonyloxy(dichloro)phenyl, etc.), etc.], or the like.

Preferable examples of "aryl substituted with protected hydroxy, with protected hydroxy and halogen, or with protected hydroxy and lower alkoxy" may be the same as above-mentioned mono-, or di-, or tri-protected hydroxy substituted phenyl; mono-, or dihalo and mono-, or di- protected hydroxy substituted phenyl; mono-, or di(lower)alkoxy and mono-, or di- protected hydroxy substituted phenyl; and mono-, or di(lower)alkyl and mono-, or di- protected hydroxy substituted phenyl.

Preferable examples of "aryl substituted with hydroxy, with hydroxy and halogen, or with hydroxy and lower alkoxy" may be the same as above-mentioned mono-, or di-, or trihydroxy phenyl; mono-, or dihydroxy and mono-, or dihalo substituted phenyl; mono-, or dihydroxy and mono-, or di(lower)alkoxy substituted phenyl; and mono-, or dihydroxy and mono-, or di(lower)alkyl substituted phenyl.

Preferable examples of "aryl substituted with acyloxy, with acyloxy and halogen, or with acyloxy and lower alkoxy" may be the same as above-mentioned mono-, or di-, or triacyloxyphenyl; mono-, or diacyloxy and mono-, or dihalo substituted phenyl; mono-, or diacyloxy and mono-, or di(lower)alkoxy substituted phenyl; and mono- or diacyloxy and mono- or di(lower)alkyl substituted phenyl.

Suitable "lower alkylene" may be a straight or branched one such as methylene, ethylene, trimethylene, tetramethylene, ethylethylene, propylene, pentamethylene, hexamethylene or the like.

Suitable "lower alkenylene" may be vinylene, propenylene, butenylene, pentenylene, butadienylene, pentadienylene or the like.

Suitable pharmaceutically acceptable salts of the object compound [I] are conventional non-toxic salts and include a metal salt such as a alkali metal salt [e.g. sodium salt, potassium salt, etc.] and an alkaline earth metal salt [e.g. calcium salt, magnesium salt, etc.], an acid addition salt such as an organic acid addition salt [e.g. formate, acetate, trifluoroacetate, fumarate, maleate, tartrate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. aspartic acid salt, glutamic acid salt, etc.] and the like.

With respect to the salts of the compounds [Ia], [Ib] and [Ic] in the Processes 2 and 3, it is to be noted that these compounds are included within the scope of the compound [I], and accordingly the suitable examples of the salts of these compounds are to be referred to those as exemplified for the object compound [I].

The processes for preparing the object compounds [I] of the present invention are explained in detail in the following.

PROCESS 1

The object compound [I] or its salt can be prepared by reacting a compound [II] or its reactive derivative at the amino group or a salt thereof with a compound [III] or its reactive derivative at the carboxy group or a salt thereof.

Suitable reactive derivative at the amino group of the compound [II] may include Schiff's base type imino or its tautomeric enamine type isomer formed by the reaction of the compound [II] with a carbonyl compound such as aldehyde, ketone or the like; a silyl derivative formed by the reaction of the compound [II] with a silyl compound such as bis(trimethylsilyl)acetamide, mono(trimethylsilyl)acetamide, bis(trimethylsilyl)urea or the like; a derivative formed by reaction of the compound [II] with phosphorus trichloride or phosgene, and the like.

Suitable salts of the compound [II] and its reactive derivative can be referred to the acid addition salt as exemplified for the compound [I].

Suitable reactive derivative at the carboxy group of the compound [III] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^{30}=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound [III] to be used.

Suitable salts of the compound [III] and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], or the like.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [III] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; diphenylphosphinic chloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

PROCESS 2

The compound [Ib] or its salt can be prepared by subjecting a compound [Ia] or its salt to elimination reaction of the hydroxy-protective group.

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, methanesulfonic acid, p-toluenesulfonic acid, etc.] and an inorganic acid [e.g. hydrochloric acid, hydrobromic acid, sulfuric acid, hydrogen chloride, hydrogen bromide, hydrogen fluoride, etc.].

The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to heating.

PROCESS 3

The object compound [Ic] or its salt can be prepared by reacting a compound [Ib] or its salt with an acylating agent.

Suitable acylating agents are the corresponding carboxylic acid or sulfonic acid compounds, which are represented by the formula: $R^2$—OH wherein $R^2$ is acyl, and reactive derivatives thereof.

Suitable "acyl" may be the same as acyl group for "acyloxy" as exemplified above.

Suitable said reactive derivatives can be referred to the ones at the carboxy groups of the compound [III] as exemplified above. The kind of such reactive derivatives can be selected depending on the kind of acyl group to be introduced.

The reaction is usually carried out in a conventional solvent, such as methylene chloride, chloroform, benzene, toluene, pyridine, diethyl ether, dioxane, tetrahydrofuran, acetone, acetonitrile, ethyl acetate, N,N-dimethylformamide or any other organic solvent which does not adversely affect the reaction. In case that the acylating agent is liquid, it can also be used as a solvent. In case that the carboxylic acid compounds are used as acylating agent in the free acid form or salt form, it is preferable to carry out the reaction in the presence of a conventional condensing agent such as N,N'-dicyclohexylcarbodiimide or the like.

The reaction temperature is not critical and the reaction can be carried out under cooling, at ambient temperature, or under heating.

This reaction is preferably carried out in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, pyridine, N-methylmorpholine or N,N-dimethylaniline.

Among the starting compounds [II] and [III], some of them are new and can be prepared by processes as illustrated in the following reaction schemes.

PROCESS A

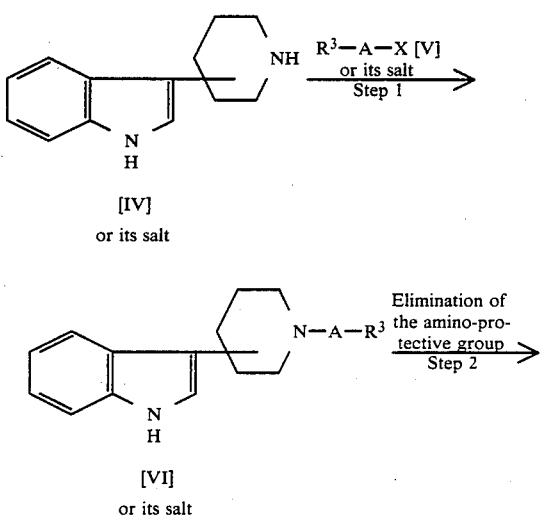

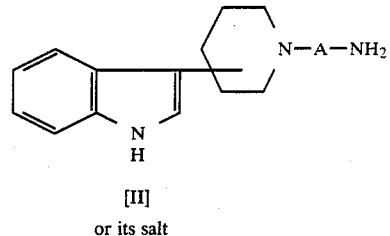

PROCESS B

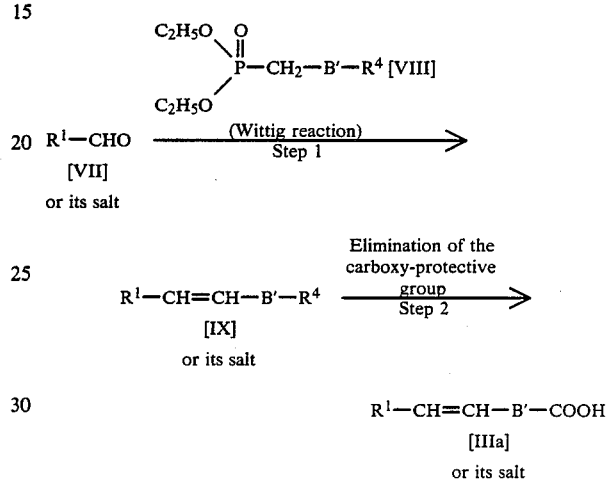

wherein
$R^3$ is protected amino,
$R^4$ is protected carboxy,
B' is lower alkylene or lower alkenylene,
X is a leaving group,
$R^1$ and A are each as defined above.

Suitable "protected amino" may be acylamino such as substituted or unsubstituted lower alkanoylamino [e.g. formylamino, acetylamino, propionylamino, trifluoroacetylamino, etc.], phthaloylimino, lower alkoxycarbonylamino [e.g. tert-butoxycarbonylamino, tert-amyloxycarbonylamino, etc.], substituted or unsubstituted aralkyloxycarbonylamino [e.g. benzyloxycarbonylamino, p-nitrobenzyloxycarbonylamino, etc.], substituted or unsubstituted arenesulfonylamino [e.g. benzenesulfonylamino, tosylamino, etc.], nitrophenylsulfenylamino, or the like, aralkylamino [e.g. tritylamino, benzylamino, etc.] or the like.

Suitable "protected carboxy" may be carboxy group protected by conventional protective group such as lower alkoxycarbonyl [e.g. methoxycarbonyl, ethoxycarbonyl, propoxycarbonyl, isopropoxycarbonyl, botoxycarbonyl, sec-butoxycarbonyl, isobutoxycarbonyl, tert-butoxycarbonyl, pentyloxycarbonyl, neopentyloxycarbonyl, hexyloxycarbonyl, etc.], optionally substituted ar(lower)alkoxycarbonyl for example, mono or di or triphenyl(lower)alkoxycarbonyl which may be substituted with nitro [e.g. benzyloxycarbonyl, 4-nitrobenzyloxycarbonyl, benzhydryloxycarbonyl, trityloxycarbonyl, etc], or the like.

Suitable "leaving group" may be an acid residue such as halogen "e.g. chlorine, bromine, fluorine and iodine], sulfonyloxy [e.g. mesyloxy, tosyloxy, phenylsulfonyloxy, etc.] or the like.

The processes for preparing the starting compounds are explained in detail in the following.

PROCESS A

Step 1

The compound [VI] or its salt can be prepared by reacting a compound [IV] or its salt with a compound [V] or its salt.

Suitable salts of the compounds [IV], [V] and [VI] can be referred to the acid addition salts as exemplified for the compound [I].

This reaction is usually carried out in a conventional solvent such as water, an alcohol [e.g. methanol, ethanol, isopropyl alcohol, etc.], dioxane, tetrahydrofuran, N,N-dimethylformamide, methylene chloride, chloroform, tetrachloromethane, or any other conventional solvent which does not adversely affect this reaction, or a mixture thereof.

The reaction is carried out at ambient temperature, under warming or under heating, although the reaction temperature is not critical.

This reaction can also be conducted in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, pyridine or N,N-dimethylaniline.

This reaction can also be performed in the presence of an alkali metal halide such as sodium iodide or potassium iodide.

Step 2

The compound [II] or its salt can be prepared by subjecting a compound [VI] or its salt to elimination reaction of the amino-protective group.

This elimination reaction can be carried out by a conventional manner, and the reaction mode [e.g. hydrolysis, reduction, etc.] and the reaction conditions [e.g. acid, base, catalyst, solvent, reaction temperature, etc.] of this reaction can be referred to those of the conventional elimination reaction of the amino-protective group.

PROCESS B

Step 1

The compound [IX] or its salt can be prepared by reacting a compound [VII] or its salt with a compound [VIII].

Suitable salts of the compounds [VII] and [IX] can be referred to the ones as exemplified for the compound [III].

This reaction is so-called Wittig reaction, and the reaction mode and reaction conditions can be referred to those of the conventional Witting reaction.

Step 2

The compound [III] or its salt can be prepared by subjecting a compound [VIII] or its salt to elimination reaction of the carboxy-protective group.

This elimination reaction can be carried out by a conventional manner, and the reaction mode [e.g. hydrolysis, reduction, etc.] and the reaction conditions [e.g. acid, base, catalyst, solvent, reaction temperature, etc.] of this reaction can be referred to those of the conventional elimination reaction of the carboxy protective group.

The compounds obtained by the above Processes 1, 2, 3, A and B can be isolated and purified by a conventional method such as pulverization, recrystallization, column chromatography, reprecipitation or the like.

It is to be noted that each of the object compound [I] and the starting compounds may include one or more stereoisomer due to asymmetric carbon atom(s) and/or carbon-carbon double bond (i.e. Z-isomer and E-isomer), and all such isomers and mixture thereof are included within the scope of this invention.

The new indolylpiperidine compound [I] and pharmaceutically acceptable salts thereof possess antiallergic activity and are useful for a therapeutic treatment or prophylaxis of allergic disease such as allergic asthma, allergic rhinitis, allergic conjunctivitis chronic urticaria, or the like.

The compound [I] and a pharmaceutically acceptable salt thereof of this invention can be used in the form of conventional solid, semisolid or liquid pharmaceutical preparations in admixture with conventional organic or inorganic carriers or excipients suitable for oral, parenteral or external application. The active ingredients may be admixed with conventional, nontoxic, pharmaceutically acceptable carriers having the form of, for example, tablets, pellets, capsules, patches, suppositories, solutions, emulsions or suspensions or any other form suitable for use. Usable carriers are not limited to any particular species. Thus, conventional carriers such as water, glucose, lactose, gum arabic, gelatin, mannitol, starch paste, magnesium trisilicate, talc, corn starch, keratin, colloidal silica, potato starch and urea and other carriers suitable for the manufacture of solid, semisolid or liquid preparations can be used. Furthermore, auxiliaries, stabilizers, thikening agents and colorants as well as aromas may be added.

The dose or therapeutically effective amount of the object compounds [I] of this invention may vary depending on the age and symptoms of each individual patient to be treated. Generally, the active ingredients are administered for disease treatment in a daily dose of about 0.1–100 mg/kg, preferably 0.1–10 mg/kg.

In order to illustrate the usefulness of the object compound [I], the pharmacological test data of some representative compounds of the compound [I] are shown in the following.

Test Compounds

Compound A: 1-[4-{5-(4-Hydroxy-3-methoxyphenyl)-(2E,4E)-2,4-pentadienoylamino}butyl]-4-(3-indolyl)piperidine Compound B: 1-[2-{5-(4-Hydroxy-3-methoxyphenyl)-(2E,4E)-2,4-pentadienoylamino}ethyl]-4-(3-indolyl)piperidine Compound C: 1-[2-{5-(4-Hydroxy-3,5-dimethoxyphenyl)-(2E,4E)-2,4-pentadienoylamino}ethyl]-4-(3-indolyl)piperidine Compound D: 1-[2-{5-(4-Acetoxy-3-methoxyphenyl)-(2E,4E)-2,4-pentadienoylamino}ethyl]-4-(3-indolyl)piperidine Compound E: 1-[2-{5-(4-Acetoxy-3,5-dimethoxyphenyl)-(2E,4E)-2,4-pentadienoylamino}ethyl]-4-(3-indolyl)piperidine Compound F: 1-[2-{5-(3,5-Dichloro-4-hydroxyphenyl)-(2E,4E)-2,4-pentadienoylamino}ethyl]-4-(3-indolyl)piperidine

TEST 1

Antagonistic action on anaphylactic asthma in guinea pigs

Male Hartley-strain guinea pigs weighing 305–400 g were used. These animals were sensitized by intravenous injection of 0.5 ml/animal of rabbit antiserum to egg-white albumin (PCA antibody titer 4,000). After 24 hours, the animals were housed individually in 5.3-liter plastic chambers. Using a commercial sprayer, a 5% egg-white albumin solution was sprayed in the form of an aerosol into each chamber at a rate of 0.16 ml/min for 2 minutes. Thirty minutes prior to the spraying of the egg-white albumin solution, the test compound was administered orally in varied concentrations. Each dosed group consisted of 5 animals. The prophylactic effect to anaphylaxis was expressed in terms of the $ED_{50}$ value determined on the basis of the number of guinea pigs which had survived for not less than 2 hours after antigen spraying for each administration concentration of the test compound.

The values thus obtained are given in the following table.

| Test Compound | Test Results Prophylactic Effect $ED_{50}$ (mg/kg) |
|---|---|
| A | 0.5 |
| C | 0.5 |

TEST 2

Anti-SRS-A activity

Peritoneal exudate cells were collected from glycogen-injected SD rats and adjusted to $1 \times 10^7$ cells/ml with Tyrode's solution. One milliliter of the cell suspension was incubated with indomethacin (10 μg/ml) and each varied concentration of the test compound for 10 minutes and, then, further incubated with $Ca^{++}$-ionophore (A23187, 1 μg/ml) for 10 minutes. The supernatant was collected by centrifugation and the SRS-A (slow-reacting substance of anaphylaxis) activity was determined in terms of contractility of the isolated guinea pig ileum in the presence of mepyramine, atropine and methysergide.

The results were expressed in terms of the 50% inhibitory concentration to SRS-A synthesis or release from peritoneal exudate cells.

| Test Compound | Test results Inhibitory Concentration $IC_{50}$ (μg/ml) |
|---|---|
| B | 0.91 |
| C | 0.68 |
| D | 0.6 |
| E | 0.23 |
| F | 0.65 |

The following Preparations and Examples are given for the purpose of illustrating the present invention in more detail.

PREPARATION 1

A mixture of 4-(3-indolyl)piperidine (7.88 g), N-(2-bromoethyl)phthalimide (10.0 g) and sodium hydrogen carbonate (3.64 g) in dry N,N-dimethylformamide (93 ml) was heated at 68°–74° C. for 4 hours. After cooling, the reaction mixture was poured into ice-water (1,000 ml). The resulting precipitate was collected by filtration and washed with methanol to give 1-(2-phthalimidoethyl)-4-(3-indolyl)piperidine (5.53 g).

NMR (DMSO-$d_6$, δ): 1.3–3.4 (11H, m), 3.77 (2H, t, J=6.0 Hz), 6.8–7.8 (5H, m), 7.89 (4H, m), 10.73 (1H, s)

MASS: 373 (M+), 213

PREPARATION 2

A mixture of 4-(3-indolyl)piperidine (7.47 g), N-(3-bromopropyl)phthalimide (10.0 g) and sodium hydrogen carbonate (3.45 g) in dry N,N-dimethylformamide (88 ml) was heated at 70° C. for 2 hours. After cooling, the reaction mixture was poured into water (880 ml) and extracted with a mixture of chloroform and methanol (10:1 V/V). The organic layer was washed with a saturated sodium chloride solution and dried over magnesium sulfate. The solvent was distilled off and the residue was subjected to column chromatography on silica gel (290 g) and eluted with a mixture of chloroform and methanol (20:1 V/V). The fractions containing the object compound were combined and concentrated under reduced pressure. The residue was triturated with diethyl ether to give pale yellow crystals of 1-(3-phthalimidopropyl)-4-(3-indolyl)-piperidine (5.83 g).

IR (Nujol): 3360, 1770, 1704, 1040, 735, 712 $cm^{-1}$

NMR (DMSO-$d_6$, δ): 1.0–3.1 (13H, m), 3.67 (2H, t, J=6.0 Hz), 6.8–7.6 (5H, m), 7.6–8.0 (4H, m), 10.63 (1H, s)

PREPARATION 3

1-(4-Phthalimidobutyl)-4-(3-indolyl)piperidine was obtained according to a similar manner to that of Preparation 2.

IR (Nujol): 3400–3300 (broad), 1770, 1700 (broad) $cm^{-1}$

PREPARATION 4

A mixture of 1-(2-phthalimidoethyl)-4-(3-indolyl)-piperidine (6.3 g) and hydrazine monohydrate (2.2 g) in ethanol (250 ml) was refluxed for 70 minutes. After cooling, the reaction mixture was filtered and the filtrate was concentrated under reduced pressure. The residue was treated with 5% sodium hydroxide solution (300 ml) and extracted with ethyl acetate (300 ml). The organic layer was washed with a saturated sodium chloride solution and dried over magnesium sulfate. The evaporation of solvent gave 1-(2-aminoethyl)-4-(3-indolyl)piperidine (3.74 g).

IR (Nujol): 3350, 1596, 953, 733 $cm^{-1}$

NMR (CDCl$_3$, δ): 1.5–3.4 (15H, m), 6.8–7.8 (5H, m), 8.5 (1H, br s)

MASS: 243 (M+), 213

PREPARATION 5

The following compounds were obtained according to a similar manner to that of Preparation 4.

(1) 1-(3-Aminopropyl)-4-(3-indolyl)piperidine IR (Nujol): 3360, 3150, 1377, 1225 $cm^{-1}$ NMR (DMSO-$d_6$, δ): 1.3–3.2 (17H, m), 6.7–7.7 (5H, m), 10.67 (1H, s)

(2) 1-(4-Aminobutyl)-4-(3-indolyl)piperidine

IR (Nujol): 3390, 3150, 1110, 897, 736 $cm^{-1}$

NMR (DMSO-$d_6$, δ): 1.0–3.2 (19H, m), 6.7–7.6 (5H, m), 10.67 (1H, s)

PREPARATION 6

A mixture of 4-hydroxy-3,5-dimethylbenzaldehyde (5 g), N,N-diisopropylethylamine (6.9 ml), (2-methoxyethoxy)methylchloride (4.26 ml) and 1,2-dichloroethane (65 ml) was refluxed for 5 hours. The reaction mixture was washed with water and dried over magnesium sulfate. After removal of the solvent, the residue was subjected to column chromatography on silica gel and eluted with a mixture of n-hexane and ethyl acetate (8:2 V/V). The fractions containing the object compound were combined and concentrated under reduced pressure to give 4-[(2-methoxyethoxy)methoxy]-3,5-dimethylbenzaldehyde (6.54 g).

IR (neat): 2900, 1690, 1600, 1130, 1100, 960, 740 cm$^{-1}$

NMR (CDCl$_3$, δ): 2.30 (6H, s), 3.32 (3H, s), 3.75, 4.0 (each 2H, m), 5.19 (2H, m), 7.60 (2H, s), 9.93 (1H, s)

PREPARATION 7

The following compounds were obtained according to a similar manner to that of Preparation 6.

(1) 3,5-Diisopropyl-4-[(2-methoxyethoxy)methoxy]-benzaldehyde

IR (Nujol): 2950, 1690, 1595, 1585, 955 cm$^{-1}$ (2) 4-[(2-Methoxyethoxy)methoxy]-3-methylbenzaldehyde IR (neat): 2950, 1690, 1600, 1590, 980 cm$^{-1}$ NMR (CDCl$_3$, δ): 2.31 (3H, s), 3.38 (3H, s), 3.6,3.8 (each, 2H, m), 5.41 (2H, s), 7.15-7.85 (3H, m), 9.90 (1H, s)

(3) 3-Chloro-4-[(2-methoxyethoxy)methoxy]benzaldehyde

IR (neat): 1700, 1595, 1570, 950 cm$^{-1}$

NMR (CDCl$_3$, δ): 3.30 (3H, m), 3.6, 3.8 (each, 2H, m), 5.53 (2H, s), 7.2-7.9 (3H, m), 9.88 (1H, s)

(4) 3,5-Dichloro-4-[(2-methoxyethoxy)methoxy]benzaldehyde

IR (neat): 2900, 1705, 1590, 1560, 920, 810 cm$^{-1}$

NMR (CDCl$_3$, δ): 3.4 (3H, s), 3.6, 4.1 (each 2H, m), 5.38 (2H, s), 7.82 (2H, s), 9.85 (1H, s)

(5) 3-Methoxy-2-[(2-methoxyethoxy)methoxy]benzaldehyde

IR (neat): 1690, 1585, 950, 850, 785, 750 cm$^{-1}$

NMR (CDCl$_3$, δ): 3.40 (3H, s), 3.6, 3.9 (each 2H, m), 3.95 (3H, s), 5.38 (2H, s), 7.2-7.6 (3H, m), 10.53 (1H, s)

MASS (m/e): 240 (M$^+$), 89, 59

(6) 3,5-Di-tert-butyl-4-[(2-methoxyethoxy)methoxy]-benzaldehyde

IR (neat): 1695, 1595, 945 cm$^{-1}$

PREPARATION 8

To a stirred suspension of 60% sodium hydride (1.01 g) in dry tetrahydrofuran (60 ml), 80% triethyl 4-phosphonocrotonate (6.57 g) was added dropwise below 10° C. under an inert atmosphere. After being stirred for 30 minutes, a solution of 4-[(2-methoxyethoxy)methoxy]-3,5-dimethylbenzaldehyde (5.0 g) in dry tetrahydrofuran (50 ml) was added thereto below 10° C. After stirring for 2 hours, the reaction mixture was concentrated under reduced pressure. The residue was dissolved in ethyl acetate (100 ml), washed with a saturated aqueous solution of sodium chloride and dried over magnesium sulfate. The solvent was distilled off and the residue was subjected to column chromatography on silica gel (130 g) and eluted with a mixture of n-hexane and ethyl acetate (7:3 V/V). The fractions containing the object compound were combined and concentrated under reduced pressure to give a syrup of ethyl 5-[4-{(2-methoxyethoxy)methoxy}-3,5-dimethylphenyl]-(2E,4E)-2,4-pentadienoate (5.28 g).

IR (neat): 2950, 1710, 1620, 1600, 970, 865 cm$^{-1}$

PREPARATION 9

The following compounds were obtained according to a similar manner to that of Preparation 8.

(1) Ethyl 5-[3,5-diisopropyl-4-{(2-methoxyethoxy)methoxy}phenyl]-(2E,4E)-2,4-pentadienoate IR (Nujol): 1710, 1625, 1595, 965, 870 cm$^{-1}$ NMR (CDCl$_3$, δ): 1.25 (12H, d, J=8 Hz), 1.31 (3H, t, J=8 Hz), 3.45 (2H, sextet, J=8 Hz), 3.43 (3H, s), 3.7, 4.0 (each 2H, m), 4.25 (2H, q, J=8 Hz), 5.03 (2H, s), 6.0 (1H, d, J=15 Hz), 6.8-7.7 (5H, m)

MASS (m/e): 362 (M$^+$), 89, 59 (base)

(2) Ethyl 5-[4-{(2-methoxyethoxy)methoxy}-3-methylphenyl]-(2E,4E)-2,4-pentadienoate NMR (CDCl$_3$, δ): 1.31 (3H, t, J=8 Hz), 2.25 (3H, s), 3.35 (3H, s), 3.7, 3.9 (each, 2H, m), 4.25 (2H, g, J=8 Hz), 5.31 (2H, s), 5.95 (1H, d, J=15 Hz), 6.7-7.7 (6H, m)

MASS (m/e): 320 (M$^+$), 276, 89, 59

(3) Ethyl 5-[3-chloro-4-{(2-methoxyethoxy)methoxy}phenyl]-(2E,4E)-2,4-pentadienoate IR (neat): 2900, 1710, 1630, 1600, 1055, 980 cm$^{-1}$ NMR (CDCl$_3$, δ): 1.31 (3H, t, J=8 Hz), 3.35 (3H, s), 3.7, 3.9 (each 2H, m), 4.28 (2H, q, J=8 Hz), 5.33 (2H, s), 5.97 (1H, d, J=15 Hz), 6.7-7.7 (6H, m)

(4) Ethyl 5-[3,5-dichloro-4-{(2-methoxyethoxy)methoxy}phenyl]-(2E,4E)-2,4-pentadienoate mp: 67°-69° C. (recrystallized from a mixture of toluene and ethyl acetate (8:1))

IR (Nujol): 1710, 1630, 1545, 1000, 925, 860, 800 cm$^{-1}$

NMR (CDCl$_3$, δ): 1.30 (3H, t, J=8 Hz), 3.38 (3H, s), 3.6, 4.1 (each 2H, m), 4.23 (2H, q, J=8 Hz), 5.29 (2H, s), 6.03 (1H, d, J=15 Hz), 6.6-7.7 (5H, m)

MASS (m/e): 376 (M+2), 375 (M+1), 374 (M$^+$), 89 (base)

(5) Ethyl 5-[3-methoxy-2-{(2-methoxyethoxy)methoxy}-phenyl]-(2E,4E)-2,4-pentadienoate mp: 48°-49° C. (recrystallized from a mixture of n-hexane and diisopropyl ether)

IR (Nujol): 1720, 1623, 1000, 945, 850 cm$^{-1}$

NMR (CDCl$_3$, δ): 1.35 (3H, t, J=7 Hz), 3.4 (3H, s), 3.6, 3.9 (each 2H, m), 3.86 (3H, s), 4.27 (2H, q, J=7 Hz), 5.25 (2H, s), 6.03 (1H, d, J=15 Hz), 6.6-7.7 (6H, m)

(6) Ethyl 5-[4-methoxy-3-{(2-methoxyethoxy)methoxy}-phenyl]-(2E,4E)-2,4-pentadienoate IR (neat): 1710, 1625, 1600, 1000 cm$^{-1}$ NMR (CDCl$_3$, δ): 1.36 (3H, t, J=7 Hz), 3.4 (3H, s), 3.6, 3.9 (each 2H, m), 3.90 (3H, s), 4.25 (2H, q, J=7 Hz), 5.31 (2H, s), 5.98 (1H, d, J=15 Hz), 6.6-7.8 (6H, m)

(7) Ethyl 5-[3,5-di-tert-butyl-4-{(2-methoxyethoxy)methoxy}phenyl]-(2E,4E)-2,4-pentadienoate IR (neat): 1710, 1625 cm$^{-1}$

PREPARATION 10

To a stirred solution of ethyl 5-[4-{(2-methoxyethoxy)methoxy}-3,5-dimethylphenyl]-(2E,4E)-2,4-pentadienoate (5.28 g) in methanol (55 ml) was added a solution of sodium hydroxide (6.32 g) in water (18 ml) below 20° C. After being stirred for an hour, the reaction mixture was concentrated under reduced pressure. The residue was dissolved in water (200 ml) and adjusted to pH 4 with 10% hydrochloride solution. The resulting precipitate was collected by filtration and washed with water to give yellowish powder of 5-[4-{(2-methoxyethoxy)methoxy}-3,5-dimethylphenyl]-(2E,4E)-2,4-pentadienoic acid (4.13 g).

mp: 88°–91° C.

IR (Nujol): 2650, 1675, 1615, 1595, 1000, 970, 860 cm$^{-1}$

NMR (CDCl$_3$, δ): 2.30 (6H, s), 3.43 (3H, s), 3.7, 4.0 (each 2H, m), 5.05 (2H, s), 5.95 (1H, d, J=15 Hz), 6.75–7.8 (5H, m), 10.25 (1H, m)

MASS (m/e): 306 (M+), 89 (base)

PREPARATION 11

The following compounds were obtained according to a similar manner to that of Preparation 10.

(1) 5-[3,5-Diisopropyl-4-{(2-methoxyethoxy)methoxy}phenyl]-(2E,4E)-2,4-pentadienoic acid mp: 96°–113° C.

IR (Nujol): 2600, 1685, 1615, 1595, 1100, 1080, 970 cm$^{-1}$

NMR (CDCl$_3$, δ): 1.25 (12H, d, J=8 Hz), 3.45 (2H, sext, J=8 Hz), 3.43 (3H, s), 3.7, 4.0 (each 2H, m), 5.03 (2H, s), 6.0 (1H, d, J=15 Hz), 6.8–7.8 (5H, m), 10.13 (1H, m)

MASS (m/e): 362 (M+), 89, 59 (base)

(2) 5-[4-{(2-Methoxyethoxy)methoxy}-3-methylphenyl]-(2E,4E)-2,4-pentadienoic acid
mp: 117°–119° C.

IR (Nujol): 2600, 1670, 1600, 1000, 930 cm$^{-1}$

NMR (CDCl$_3$, δ): 2.26 (3H, s), 3.30 (3H, s), 3.6, 3.9 (each, 2H, m), 5.32 (2H, s), 5.98 (1H, d, J=15 Hz), 6.7–7.8 (6H, m), 8.7 (1H, m)

(3) 5-[3-Chloro-4-{(2-methoxyethoxy)methoxy}phenyl]-(2E,4E)-2,4-pentadienoic acid
mp: 130°–135° C.

IR (Nujol): 2600, 1680, 1615, 1590, 1050, 995 cm$^{-1}$

NMR (CDCl$_3$, δ): 3.30 (3H, s), 3.6, 3.9 (each 2H, m), 5.38 (2H, s), 6.01 (1H, d, J=15 Hz), 6.7–7.7 (6H, m), 9.7 (1H, m)

(4) 5-[3,5-Dichloro-4-{(2-methoxyethoxy)methoxy}phenyl]-(2E,4E)-2,4-pentadienoic acid
mp: 116°–120° C.

IR (Nujol): 2600, 1690, 1630, 990, 905, 805 cm$^{-1}$

NMR (CDCl$_3$, δ): 3.40 (3H, s), 3.6, 4.1 (each 2H, m), 5.29 (2H, s), 6.05 (1H, d, J=15 Hz), 6.7–7.7 (5H, m), 9.65 (1H, br)

MASS (m/e): 348 (M+2), 346 (M+), 89, 59 (base)

(5) 5-[3-Methoxy-2-{(2-methoxyethoxy)methoxy}phenyl]-(2E,4E)-2,4-pentadienoic acid
mp: 140°–144° C.

IR (Nujol): 2600, 1690, 1610, 1050, 955 cm$^{-1}$

NMR (CDCl$_3$, δ): 3.33 (3H, s), 3.5, 3.8 (each 2H, m), 3.80 (3H, s), 5.15 (2H, s), 5.93 (1H, d, J=15 Hz), 6.7–7.7 (6H, m), 9.5 (1H, br)

(6) 5-[4-Methoxy-3-{(2-methoxyethoxy)methoxy}phenyl]-(2E,4E)-2,4-pentadienoic acid
mp: 121°–125° C.

IR (Nujol): 2600, 1670, 1620, 1590 cm$^{-1}$

NMR (CDCl$_3$, δ): 3.35 (3H, s), 3.55, 3.90 (each 2H, m), 3.86 (3H, s), 5.30 (2H, s), 5.92 (1H, d, J=15 Hz), 6.7–7.7 (6H, m), 10.2 (1H, br)

(7) 5-[3,5-Di-tert-butyl-4-{(2-methoxyethoxy)methoxy}phenyl]-(2E,4E)-2,4-pentadienoic acid IR (Nujol): 2650, 1680, 1620, 970 cm$^{-1}$ NMR (CDCl$_3$, δ): 1.46 (18H, s), 3.42 (3H, s), 3.66, 3.96 (each 2H, m), 5.0 (2H, s), 5.97 (1H, d, J=15.5 Hz), 6.6–7.7 (5H, m), 9.2 (1H, br)

EXAMPLE 1

To a stirred mixture of 3-[3-methoxy-4-{(2-methoxyethoxy)methoxy}phenyl]-(E)-propenoic acid (1.75 g) and triethylamine (1.81 ml) in dry N,N-dimethylformamide (10 ml) was added slowly diphenyl phosphinic chloride (1.47 g) at −10° to −15° C. under an inert atmosphere. After being stirred for 30 minutes, a solution of 1-(2-aminoethyl)-4-(3-indolyl)piperidine (1.5 g) in dry N,N-dimethylformamide (10 ml) was added slowly to the reaction mixture at −10° C. After being stirred for 1 hour at ambient temperature, the reaction mixture was poured into ice-water (200 ml) and extracted with chloroform (100 ml). The extract was washed with a saturated sodium chloride solution and dried over magnesium sulfate. The solvent was distilled off and the residue was subjected to column chromatography on silicagel (47 g) and eluted with a mixture of chloroform and methanol (10:1). The fractions containing the object compound were combined and concentrated under reduced pressure to give syrup of 1-[2-[3-[3-methoxy-4-{(2-methoxyethoxy)methoxy}phenyl]-(E)-propenoylamino]ethyl]-4-(3-indolyl)piperidine (2.8 g).

NMR (CDCl$_3$, δ): 1.6–3.3 (11H, m), 3.37 (3H, s), 3.55 (4H, m), 3.85 (2H, m), 3.89 (3H, s), 5.32 (2H, s), 6.35 (1H, d, J=15.0 Hz), 6.52 (1H, br s), 6.9–7.8 (8H, m), 7.57 (1H, d, J=15.0 Hz), 8.25 (1H, br s)

EXAMPLE 2

The following compounds were obtained according to a similar manner to that of Example 1.

(1) 1-[2-[5-[3-Methoxy-4-{(2-methoxyethoxy)methoxy}phenyl]-(2E,4E)-2,4-pentadienoylamino]ethyl]-4-(3-indolyl)piperidine IR (Nujol): 3300, 1660, 1260, 1092, 990, 744 cm$^{-1}$ NMR (CDCl$_3$, δ): 1.6–3.3 (11H, m), 3.35 (3H, s), 3.54 (4H, m), 3.84 (2H, m), 3.86 (3H, s), 5.30 (2H, s), 6.07 (1H, d, 15.0 Hz), 6.70–7.80 (12H, m), 9.30 (1H, s)

MASS: 533 (M+), 213

(2) 1-[3-[5-[3-Methoxy-4-{(2-methoxyethoxy)methoxy}phenyl]-(2E,4E)-2,4-pentadienoylamino]propyl]-4-(3-indolyl)piperidine NMR (CDCl$_3$, δ): 1.5–3.6 (15H, m), 3.36 (3H, s), 3.6 (2H, m), 3.87 (3H, s), 3.90 (2H, m), 5.35 (2H, s), 6.02 (1H, d, J=14.4 Hz), 6.6–7.9 (12H, m), 8.55 (1H, s)

MASS: 547 (M+)

(3) 1-[4-[5-[3-Methoxy-4-{(2-methoxyethoxy)methoxy}phenyl]-(2E,4E)-2,4-pentadienoylamino]butyl]-4-(3-indolyl)piperidine IR (Nujol): 3400, 3200 (broad), 1650, 1377, 1260 cm$^{-1}$ NMR (CDCl$_3$, δ): 1.3–3.4 (17H, m), 3.33 (3H, s), 3.55 (2H, m), 3.80 (5H, br s), 5.27 (2H, s), 6.11 (1H, d, J=15.0 Hz), 6.5–8.0 (12H, m), 9.23 (1H, s)

MASS: 561 (M+)

(4) 1-[2-{5-(3,4-Dimethoxyphenyl)-(2E,4E)-2,4-pentadienoylamino}ethyl]-4-(3-indolyl)piperidine
mp: 196°–198° C. (recrystallized from ethanol)

IR (Nujol): 3280, 1640, 1610, 1590, 1550, 1510 cm$^{-1}$

NMR (DMSO-d$_6$, δ): 1.4–3.5 (13H, m), 3.78 (3H, s), 3.81 (3H, s), 6.15 (1H, d, J=15.0 Hz), 6.8–7.6 (11H, m), 7.99 (1H, br t), 10.75 (1H, br s)

MASS: 459 (M+), 213

Elemental analysis: C$_{28}$H$_{33}$N$_3$O$_3$
Calcd.: C 73.18, H 7.24, N 9.14
Found: C 73.84, H 7.42, N 8.72

(5) 1-[2-{5-(3,4,5-Trimethoxyphenyl)-(2E,4E)-2,4-pentadienoylamino}ethyl]-4-(3-indolyl)piperidine
mp: 86°–100° C.

IR (Nujol): 3250, 1650, 1610, 1580 cm$^{-1}$

NMR (DMSO-d$_6$, δ): 1.4–3.6 (13H, m), 3.70 (3H, s), 3.83 (6H, s), 6.19 (1H, d, J=15.0 Hz), 6.7–7.7 (10H, m), 8.02 (1H, br t), 10.74 (1H, br s)

MASS: 489 (M+) 289, 213

Elemental analysis: $C_{29}H_{35}N_3O_4 \cdot \frac{3}{4}H_2O$
Calcd.: C 69.23, H 7.31, N 8.35
Found: C 69.38, H 7.08, N 8.40

(6) 1-[2-{3-(4-Hydroxy-3-methoxyphenyl)-(E)-propenoylamino}ethyl]-4-(3-indolyl)piperidine
mp: 115°–135° C.
IR (Nujol): 3300 (broad), 1655, 1588, 1512 cm$^{-1}$ (7) 1-[2-{5-(4-Hydroxy-3-methoxyphenyl)-(2E,4E)-2,4-pentadienoylamino}ethyl]-4-(3-indolyl)piperidine
mp: 115°–131° C.
IR (Nujol): 3330 (broad), 1660, 1377 cm$^{-1}$ (8) 1-[3-{5-(4-Hydroxy-3-methoxyphenyl)-(2E,4E)-2,4-pentadienoylamino}propyl]-4-(3-indolyl)piperidine
mp: 150°–170° C.
IR (Nujol): 3400, 3200 (broad), 1638, 1580 cm$^{-1}$ (9) 1-[4-{5-(4-Hydroxy-3-methoxyphenyl)-(2E,4E)-2,4-pentadienoylamino}butyl]-4-(3-indolyl)piperidine
mp: 150°–170° C.
IR (Nujol): 3200 (broad), 1640, 1580, 1270, 735 cm$^{-1}$

(10) 1-[2-[5-[3,4-Bis{(2-methoxyethoxy)methoxy}phenyl]-(2E,4E)-2,4-pentadienoylamino]ethyl]-4-(3-indolyl)piperidine
This compound was used as a starting compound of Example 7-(4) without purification.

(11) 1-[2-[5-[3,5-Dimethoxy-4-{(2-methoxyethoxy)methoxy}phenyl]-(2E,4E)-2,4-pentadienoylamino]ethyl]-4-(3-indolyl)piperidine
IR (Nujol): 3300, 1650, 1610, 1580, 1125, 990, 960, 845, 745 cm$^{-1}$

(12) 1-[3-[5-[3,5-Dimethoxy-4-{(2-methoxyethoxy)methoxy}phenyl]-(2E,4E)-2,4-pentadienoylamino]propyl]-4-(3-indolyl)piperidine
IR (neat): 3300, 3000, 2990, 1650, 1615, 1580, 1130, 990, 960, 850 cm$^{-1}$

(13) 1-[4-[5-[3,5-Dimethoxy-4-{(2-methoxyethoxy)methoxy}phenyl]-(2E,4E)-2,4-pentadienoylamino]butyl]-4-(3-indolyl)piperidine
IR (neat): 2900, 1650, 1610, 1580, 1550, 1120, 960, 850, 740 cm$^{-1}$

(14) 1-[2-[5-[4-{(2-Methoxyethoxy)methoxy}-3,5-dimethylphenyl]-(2E,4E)-2,4-pentadienoylamino]ethyl]-4-(3-indolyl)piperidine
mp: 163°–164° C. (recrystallized from ethyl acetate)
IR (Nujol): 3450, 3300, 1645, 1615, 990, 970 cm$^{-1}$
NMR (DMSO-d$_6$, δ): 1.5–2.3 (6H, m), 2.34 (6H, s), 2.5–3.1 (7H, m), 3.25 (3H, s), 3.5, 3.8 (each 2H, m), 5.05 (2H, s), 6.15 (1H, d, J=15 Hz), 6.8–7.7 (10H, m), 8.03 (1H, m), 10.7 (1H, m)
MASS (m/e): 531 (M$^+$), 213 (base)

(15) 1-[2-[5-[3,5-Diisopropyl-4-{(2-methoxyethoxy)methoxy}phenyl]-(2E,4E)-2,4-pentadienoylamino]ethyl]-4-(3-indolyl)piperidine
IR (neat): 1660, 1650, 1615, 970 cm$^{-1}$

(16) 1-[2-[5-[4-{(2-Methoxyethoxy)methoxy}-3-methylphenyl]-(2E,4E)-2,4-pentadienoylamino]ethyl]-4-(3-indolyl)piperidine
mp: 140°–144° C.
IR (Nujol): 3470, 3280, 1640, 1610, 1595, 1000, 980 cm$^{-1}$
NMR (CDCl$_3$, δ): 1.6–3.2 (13H, m), 2.25 (3H, s), 3.38 (3H, s), 3.6, 3.8 (each, 2H, m), 5.32 (2H, s), 5.96 (1H, d, J=15 Hz), 6.2–7.8 (11H, m), 8.25 (1H, m)
MASS (m/e): 517 (M$^+$), 213 (base)

(17) 1-[2-[5-[3-Chloro-4-{(2-methoxyethoxy)methoxy}phenyl]-(2E,4E)-2,4-pentadienoylamino]ethyl]-4-(3-indolyl)piperidine
IR (Nujol): 3450, 3300, 1645, 1610, 1050, 990 cm$^{-1}$
NMR (DMSO-d$_6$, δ): 1.5–2.5 (6H, m), 2.8–3.2 (7H, m), 3.65 (3H, s), 3.6, 3.8 (each 2H, m), 5.39 (2H, s), 6.10 (1H, d, J=15 Hz), 6.8–7.9 (11H, m), 8.05 (1H, m), 10.75 (1H, m)
MASS (m/e): 537, 213 (base)

(18) 1-[2-{5-(3,4-Dihydroxyphenyl)-(2E,4E)-2,4-pentadienoylamino}ethyl]-4-(3-indolyl)piperidine
IR (Nujol): 3400, 3350, 1650, 1585, 1520 cm$^{-1}$
MASS (m/e): 431 (M$^+$), 213 (base)

(19) 1-[2-{5-(4-Hydroxy-3,5-dimethoxyphenyl)-(2E,4E)-2,4-pentadienoylamino}ethyl]-4-(3-indolyl)piperidine
IR (Nujol): 3420, 1665, 1650, 1620, 1590, 1530, 1515, 1120 cm$^{-1}$
MASS (m/e): 475 (M$^+$), 213

(20) 1-[4-{5-(4-Hydroxy-3,5-dimethoxyphenyl)-(2E,4E)-2,4-pentadienoylamino}butyl]-4-(3-indolyl)piperidine
IR (Nujol): 3250, 1640, 1600, 1540, 1510, 1130, 1110, 810 cm$^{-1}$

(21) 1-[3-{5-(4-Hydroxy-3,5-dimethoxyphenyl)-(2E,4E)-2,4-pentadienoylamino}propyl]-4-(3-indolyl)piperidine
IR (Nujol): 3420, 1658, 1610, 1575, 1550, 1510, 1120 cm$^{-1}$
MASS (m/e): 489 (M$^+$), 239, 233, 213 (base), 197

(22) 1-[2-{5-(4-Acetoxy-3-methoxyphenyl)-(2E,4E)-2,4-pentadienoylamino}ethyl]-4-(3-indolyl)piperidine
IR (Nujol): 3440, 3250, 1760, 1655, 1620, 1560, 1505 cm$^{-1}$
MASS (m/e): 487 (M$^+$), 213 (base)

(23) 1-[2-{5-(3-Methoxy-4-propionyloxyphenyl)-(2E,4E)-2,4-pentadienoylamino}ethyl]-4-(3-indolyl)piperidine
IR (Nujol): 3430, 3250, 3060, 1750, 1655, 1620, 1560 cm$^{-1}$
MASS (m/e): 501 (M$^+$), 213 (base)

(24) 1-[2-{5-(4-Ethoxycarbonyloxy-3,5-dimethoxyphenyl)-(2E,4E)-2,4-pentadienoylamino}ethyl]-4-(3-indolyl)piperidine
IR (Nujol): 3360, 3300, 1750, 1640, 1590, 1130, 1000, 735 cm$^{-1}$
MASS (m/e): 547 (M$^+$), 228, 213 (base)

(25) 1-[4-{5-(4-Ethoxycarbonyloxy-3,5-dimethoxyphenyl)-(2E,4E)-2,4-pentadienoylamino}butyl]-4-(3-indolyl)piperidine
IR (Nujol): 3380, 3250, 1750, 1655, 1620, 1595, 1555, 1130, 1050, 1000, 735 cm$^{-1}$
MASS (m/e): 575 (M$^+$), 531, 503, 285, 233, 213 (base)

(26) 1-[2-{5-(4-Hydroxy-3,5-dimethylphenyl)-(2E,4E)-2,4-pentadienoylamino}ethyl]-4-(3-indolyl)piperidine
IR (Nujol): 3300, 1640, 1590, 1545, 990, 860 cm$^{-1}$
MASS (m/e): 443 (M$^+$), 213 (base)

(27) 1-[2-{5-(4-Hydroxy-3,5-diisopropylphenyl)-(2E,4E)-2,4-pentadienoylamino}ethyl]-4-(3-indolyl)piperidine
IR (Nujol): 3400, 3300, 1650, 1630, 1585, 995, 870 cm$^{-1}$
MASS (m/e): 499 (M$^+$), 226, 213 (base)

(28) 1-[2-{5-(4-Hydroxy-3-methylphenyl)-(2E,4E)-2,4-pentadienoylamino}ethyl]-4-(3-indolyl)piperidine
IR (Nujol): 3200, 1640, 1575, 1550, 1000 cm$^{-1}$
MASS (m/e): 429 (M$^+$), 213 (base)

(29) 1-[2-{5-(3-Chloro-4-hydroxyphenyl)-(2E,4E)-2,4-pentadienoylamino}ethyl]-4-(3-indolyl)piperidine
IR (Nujol): 3420, 1650, 1590, 1000 cm$^{-1}$
MASS (m/e): 449 (M$^+$), 213 (base)

(30) 1-[2-{5-(4-Acetoxy-3,5-dimethoxyphenyl)-(2E,4E)-2,4-pentadienoylamino}ethyl]-4-(3-indolyl)piperidine IR (Nujol): 3380, 3320, 1755, 1650, 1620, 1595, 990, 745 cm$^{-1}$ MASS (m/e): 517 (M$^+$), 213 (base)

(31) 1-[2-[5-[3,5-Dichloro-4-{(2-methoxyethoxy)methoxy}phenyl]-(2E,4E)-2,4-pentadienoylamino]ethyl]-4-(3-indolyl)piperidine IR (neat): 1655, 1610, 995 cm$^{-1}$

(32) 1-[2-[5-[3-Methoxy-2-{(2-methoxyethoxy)methoxy}phenyl]-(2E,4E)-2,4-pentadienoylamino]ethyl]-4-(3-indolyl)piperidine IR (neat): 1650, 1610, 1000, 960 cm$^{-1}$

(33) 1-[2-[5-[4-Methoxy-3-{(2-methoxyethoxy)methoxy}phenyl]-(2E,4E)-2,4-pentadienoylamino]ethyl]-4-(3-indolyl)piperidine mp: 135°–136° C. (recrystallized from ethyl acetate)

IR (Nujol): 3260, 1640, 1615, 1595, 1550, 1510 cm$^{-1}$

NMR (DMSO-d$_6$, δ): 3.75 (3H, s), 5.23 (2H, s), 6.11 (1H, d, J=15 Hz), 6.7–7.6 (11H, m), 7.96 (1H, t like), 10.7 (1H, br)

MASS (m/e): 533, 445, 333, 213 (base)

(34) 1-[2-[5-[3,5-Di-tert-butyl-2-{(2-methoxyethoxy)methoxy}phenyl]-(2E,4E)-2,4-pentadienoylamino]ethyl]-4-(3-indolyl)piperidine mp: 98°–103° C. (recrystallized from ethanol)

IR (Nujol): 3300, 1650, 1600, 970 cm$^{-1}$

NMR (CDCl$_3$, δ): 1.42 (18H, s), 1.6–2.3 (6H, m), 2.53 (2H, t, J=7 Hz), 2.8 (3H, m), 3.35 (3H, s), 3.5 (2H, m), 3.66, 3.96 (each 2H, m), 4.93 (2H, s), 5.95 (1H, d, J=15.5 Hz), 6.17 (1H, t like), 6.6–7.7 (10H, m), 8.2 (1H, s)

(35) 1-[2-{5-(3,5-Di-tert-butyl-4-hydroxyphenyl)-(2E,4E)-2,4-pentadienoylamino}ethyl]-4-(3-indolyl)piperidine IR (Nujol): 3550, 3300, 3230, 1650, 1610, 1590, 1000 cm$^{-1}$ MASS (m/e): 527 (M$^+$), 226, 213

(36) 1-[2-{5-(3,5-Dichloro-4-hydroxyphenyl)-(2E,4E)-2,4-pentadienoylamino}ethyl]-4-(3-indolyl)piperidine MASS (m/e): 485 (M+2), 483 (M$^+$), 213 (base)

(37) 1-[2-{5-(2-Hydroxy-3-methoxyphenyl)-(2E,4E)-2,4-pentadienoylamino}ethyl]-4-(3-indolyl)piperidine IR (Nujol): 3400, 3240, 1650, 1605, 1600, 1530, 1090, 1005 cm$^{-1}$ MASS (m/e): 445 (M$^+$), 226, 213 (base)

(38) 1-[2-{5-(3-Hydroxy-4-methoxyphenyl)-(2E,4E)-2,4-pentadienoylamino}ethyl]-4-(3-indolyl)piperidine IR (Nujol): 3350, 1650, 1615, 1590 cm$^{-1}$ MASS (m/e): 445 (M$^+$), 213 (base)

(39) 1-[2-[5-{3,4-bis(Ethoxycarbonyloxy)phenyl}-(2E,4E)-2,4-pentadienoylamino]ethyl]-4-(3-indolyl)piperidine IR (Nujol): 3500, 3350, 1775, 1650, 1620, 1000 cm$^{-1}$ MASS (m/e): 529 (M+-46), 457, 285 (base), 213

EXAMPLE 3

To a solution of 1-[2-[5-[3,5-di-tert-butyl-4-{(2-methoxyethoxy)methoxy}phenyl]-(2E,4E)-2,4-pentadienoylamino]ethyl]-4-(3-indolyl)piperidine (0.5 g) in methanol (5 ml) was added dropwise methanesulfonic acid (0.26 ml) at 18°–25° C. After 2 hours the reaction mixture was adjusted to pH 7.5 with 2N-sodium hydroxide and then poured into saturated sodium bicarbonate solution (50 ml). The resulting precipitate was collected and washed with water. The precipitate was subjected to column chromatography on silica gel and eluted with a mixture of chloroform and methanol (20:1, V/V). The fractions containing the object compound were combined and concentrated under reduced pressure. The residue was recrystallized from 1,4-dioxane, to give white crystals of 1-[2-{5-(3,5-di-tert-butyl-4-hydroxyphenyl)-(2E,4E)-2,4-pentadienoylamino}ethyl]-4-(3-indolyl)piperidine (0.28 g).

mp: 108°–115° C.

IR (Nujol): 3550, 3300, 3230, 1650, 1610, 1590, 1000 cm$^{-1}$

NMR (CDCl$_3$, δ): 1.43 (18H, s), 1.6–2.3 (6H, m), 2.53 (2H, t, J=7 Hz), 2.7–3.2 (3H, m), 3.45 (2H, m), 5.33 (1H, s), 5.93 (1H, d, J=15.5 Hz), 6.15 (1H, t like), 6.65–7.7 (10H, m), 8.16 (1H, s)

MASS (m/e): 527 (M$^+$), 226, 213

EXAMPLE 4

To a stirred solution of 1-[2-[5-[3,5-dimethoxy-4-{(2-methoxyethoxy)methoxy}phenyl]-(2E,4E)-2,4-pentadienoylamino]ethyl]-4-(3-indolyl)piperidine (10.0 g) in methanol (100 ml) was added slowly methanesulfonic acid (2.3 ml) at ambient temperature. After stirring for 2 hours, the reaction mixture was adjusted to pH 7.2 with aqueous 2N sodium hydroxide solution, and poured into a solution of 4.5 g of sodium bicarbonate in 500 ml of water. After stirring for 30 minutes, the resulting precipitate was collected by filtration and washed with 100 ml of water. The residue was subjected to column chromatography on silica gel and eluted with a mixture of chloroform and methanol. The fractions containing the object compound were combined and concentrated under reduced pressure. The residue was recrystallized from ethanol to give 1-[2-{5-(4-hydroxy-3,5-dimethoxyphenyl)-(2E,4E)-2,4-pentadienoylamino}ethyl]-4-(3-indolyl)piperidine (6.69 g).

mp: 199°–202° C. (dec.)

IR (Nujol): 3420, 1665, 1650, 1620, 1590, 1530, 1515, 1120 cm$^{-1}$

NMR (DMSO-d$_6$, δ): 1.5–2.4 (7H, m), 2.7–3.5 (6H, m), 3.81 (6H, s), 6.15 (1H, d, J=14 Hz), 6.8–7.8 (10H, m), 8.0 (1H, t like), 8.68 (1H, m), 10.75 (1H, s)

MASS (m/e): 475 (M$^+$), 213

Elemental analysis: C$_{28}$H$_{33}$N$_3$O$_4$

Calcd.: C 70.71, H 6.99, N 8.83

Found: C 70.34, H 6.56, N 8.65

EXAMPLE 5

A mixture of 1-[3-[5-[3,5-dimethoxy-4-{(2-methoxyethoxy)methoxy}phenyl]-(2E,4E)-2,4-pentadienoylamino]propyl]-4-(3-indolyl)piperidine (1.67 g) and p-toluenesulfonic acid monohydrate (0.64 g) in methanol (33 ml) was refluxed for 30 minutes under an inert atmosphere. Upon cooling to ambient temperature, the mixture was added dropwise to an aqueous sodium carbonate solution. The resulting powder was subjected to column chromatography on silica gel and eluted with a mixture of chloroform and methanol (10:1 V/V). The fractions containing the object compound were combined and concentrated under reduced pressure. The obtained residue was recrystallized from a mixture of ethanol and water (7:3 V/V) to give 1-[3-{5-(4-hydroxy-3,5-dimethoxyphenyl)-(2E,4E)-2,4-pentadienoylamino}propyl]-4-(3-indolyl)piperidine (0.51 g).

mp: 176°–179° C. (recrystallized from 4 ethanol-water (8:2, V/V))

IR (Nujol): 3420, 1658, 1610, 1575, 1550, 1510, 1120 cm$^{-1}$

NMR (DMSO-d$_6$, δ): 1.4–2.5 (9H, m), 2.6–3.5 (6H, m), 3.79 (6H, s), 6.10 (1H, d, J=15 Hz), 6.7–7.7 (10H, m), 8.05 (1H, t like), 8.7 (1H, m), 10.72 (1H, s)

MASS (m/e): 489 (M$^+$), 239, 233, 213 (base), 197

Elemental analysis: C$_{29}$H$_{35}$N$_3$O$_4$

Calcd.: C 71.14, H 7.20, N 8.58
Found: C 70.79, H 7.12, N 8.57

EXAMPLE 6

A mixture of 1-[2-[3-[3-methoxy-4-{(2-methoxyethoxy)methoxy}phenyl]-(E)-propenoylamino]ethyl]-4-(3-indolyl)piperidine (2 g) and p-toluenesulfonic acid monohydrate (1.05 g) in methanol (40 ml) was refluxed for 30 minutes under an inert atmosphere. After the solvent was removed under reduced pressure, the residue was treated with water (100 ml), adjusted to pH 10.0 with a sodium carbonate solution and extracted with ethyl acetate. The extract was washed with a saturated sodium chloride solution and dried over magnesium sulfate. After removal of the solvent, the residue was subjected to column chromatography on silica gel (31 g) and eluted with a mixture of chloroform and methanol (8:1 V/V). The fractions containing the object compound were combined and concentrated under reduced pressure to give 1-[2-{3-(4-hydroxy-3-methoxyphenyl)-(E)-propenoylamino}ethyl]-4-(3-indolyl)-piperidine (0.89 g).

mp: 115°–135° C.
IR (Nujol): 3300 (broad), 1655, 1588, 1512 cm$^{-1}$
NMR (DMSO-d$_6$, δ): 1.5–3.6 (14H, m), 3.83 (3H, s), 6.50 (1H, d, J=15.0 Hz), 6.7–7.7 (9H, m), 7.83 (1H, br t), 10.70 (1H, s)
MASS: 419 (M+), 213
Elemental analysis: C$_{25}$H$_{29}$N$_3$O$_3$·½H$_2$O
Calcd.: C 70.00, H 7.06, N 9.80
Found: C 70.18, H 6.92, N 9.85

EXAMPLE 7

The following compounds were obtained according to similar manners to those of Examples 3 to 6.

(1) 1-[2-{5-(4-Hydroxy-3-methoxyphenyl)-(2E,4E)-2,4-pentadienoylamino}ethyl]-4-(3-indolyl)piperidine
mp: 115°–131° C.
IR (Nujol): 3330 (broad), 1660, 1377 cm$^{-1}$
NMR (DMSO-d$_6$, δ): 1.5–3.6 (13H, m), 3.82 (3H, s), 6.07 (1H, d, J=15.0 Hz), 6.6–7.6 (8H, m), 7.90 (1H, br t), 9.20 (1H, s), 10.68 (1H, s)
MASS: 445 (M+), 213
Elemental analysis: C$_{27}$H$_{31}$N$_3$O$_3$·½H$_2$O
Calcd.: C 71.34, H 7.10, N 9.24
Found: C 71.15, H 6.87, N 9.19

(2) 1-[3-{5-(4-Hydroxy-3-methoxyphenyl)-(2E,4E)-2,4-pentadienoylamino}propyl]-4-(3-indolyl)piperidine
mp: 150°–170° C.
IR (Nujol): 3400, 3200 (broad), 1638, 1580 cm$^{-1}$
NMR (DMSO-d$_6$, δ): 1.5–3.8 (15H, m), 3.86 (3H, s), 4.20 (1H, broad), 6.15 (1H, d, J=14.0 Hz), 6.6–7.8 (11H, m), 8.26 (1H, br s), 10.82 (1H, s)
MASS: 459 (M+), 213
Elemental analysis: C$_{28}$H$_{33}$N$_3$O$_3$·½CHCl$_3$·½C$_2$H$_5$OC$_2$H$_5$
Calcd.: C 65.85, H 6.97, N 7.55
Found: C 65.67, H 7.18, N 7.87

(3) 1-[4-{5-(4-Hydroxy-3-methoxyphenyl)-(2E,4E)-2,4-pentadienoylamino}butyl]-4-(3-indolyl)piperidine
mp: 150°–170° C.
IR (Nujol): 3200 (broad), 1640, 1580, 1270, 735 cm$^{-1}$
NMR (DMSO-d$_6$, δ): 1.2–3.7 (17H, m), 3.80 (3H, s), 6.07 (1H, d, J=15.0 Hz), 6.6–7.8 (11H, m), 8.10 (1H, s), 9.25 (1H, s), 10.82 (1H, s)
MASS: 473 (M+), 213
Elemental analysis: C$_{29}$H$_{35}$N$_3$O$_3$·½CHCl$_3$·½C$_2$H$_5$OC$_2$H$_5$
Calcd.: C 66.33, H 7.16, N 7.37
Found: C 66.02, H 7.47, N 7.33

(4) 1-[2-{5-(3,4-Dihydroxyphenyl)-(2E,4E)-2,4-pentadienoylamino}ethyl]-4-(3-indolyl)piperidine
mp: 138°–158° C. (dec.) (recrystallized from ethanol-water (8:2 V/V))
IR (Nujol): 3400, 3350, 1650, 1585, 1520 cm$^{-1}$
NMR (DMSO-d$_6$, δ): 1.5–3.6 (13H, m), 6.13 (1H, d, J=15 Hz), 6.63–7.70 (11H, m), 7.93 (1H, m), 10.73 (1H, br)
MASS (m/e): 431 (M+), 213 (base)
Elemental analysis: C$_{26}$H$_{29}$N$_3$O$_3$·6/5 ethanol
Calcd.: C 70.07, H 7.49, N 8.63
Found: C 69.77, H 7.39, N 8.67

(5) 1-[4-{5-(4-Hydroxy-3,5-dimethoxyphenyl)-(2E,4E)-2,4-pentadienoylamino}butyl]-4-(3-indolyl)piperidine
IR (Nujol): 3250, 1640, 1600, 1540, 1510, 1130, 1110, 810 cm$^{-1}$ (6) 1-[2-{5-(4-Hydroxy-3,5-dimethylphenyl)-(2E,4E)-2,4-pentadienoylamino}ethyl]-4-(3-indolyl)piperidine
mp: 125°–135° C. (recrystallized from ethanol-water (8:2 V/V))
IR (Nujol): 3300, 1640, 1590, 1545, 990, 860 cm$^{-1}$
NMR (DMSO-d$_6$, δ): 1.4–2.4 (6H, m), 2.19 (6H, s), 2.6–3.2 (7H, m), 6.11 (1H, d, J=15 Hz), 6.7–7.6 (10H, m), 7.95 (1H, m), 10.82 (1H, m)
MASS (m/e): 443 (M+), 213 (base)
Elemental analysis: C$_{28}$H$_{33}$N$_3$O$_2$·4/3H$_2$O
Calcd.: C71.92, H 7.69, N 8.99
Found: C 72.00, H 7.69, N 8.88

(7) 1-[2-{5-(4-Hydroxy-3,5-diisopropylphenyl)-(2E,4E)-2,4-pentadienoylamino}ethyl]-4-(3-indolyl)piperidine
mp: 110°–120° C. (recrystallized from ethanol-water (8:2 V/V))
IR (Nujol): 3400, 3300, 1650, 1630, 1585, 995, 870 cm$^{-1}$
NMR (DMSO-d$_6$, δ): 1.28 (12H, d, J=8 Hz), 1.5–2.4 (6H, m), 2.7–3.6 (9H, m), 6.13 (1H, d, J=15 Hz), 6.8–7.6 (10H, m), 7.95 (1H, m), 8.4 (1H, m), 10.73 (1H, m)
MASS (m/e): 499 (M+), 226, 213 (base)
Elemental analysis: C$_{32}$H$_{41}$N$_3$O$_2$·H$_2$O
Calcd.: C 74.24, H 8.37, N 8.11
Found: C 73.84, H 8.42, N 7.97

(8) 1-[2-{5-(4-Hydroxy-3-methylphenyl)-(2E,4E)-2,4-pentadienoylamino}ethyl]-4-(3-indolyl)piperidine
mp: 138°–141° C. (recrystallized from a mixture of ethanol-water (8:2 V/V))
IR (Nujol): 3200, 1640, 1575, 1550, 1000 cm$^{-1}$
NMR (DMSO-d$_6$, δ): 1.5–3.6 (13H, m), 2.20 (3H, s), 6.10 (1H, d, J=15 Hz), 6.7–7.7 (11H, m), 7.93 (1H, m), 9.65 (1H, m), 10.73 (1H, m)
MASS (m/e): 429 (M+), 213 (base)
Elemental analysis: C$_{27}$H$_{31}$N$_3$O$_2$·5/4H$_2$O
Calcd.: C 71.73, H 7.47, N 9.29
Found: C 71.78, H 7.73, N 9.28

(9) 1-[2-{5-(3-Chloro-4-hydroxyphenyl)-(2E,4E)-2,4-pentadienoylamino}ethyl]-4-(3-indolyl)piperidine
mp: 139°–155° C. (recrystallized from ethanol-water)
IR (Nujol): 3420, 1650, 1590, 1000 cm$^{-1}$
NMR (DMSO-d$_6$, δ): 1.5–3.5 (13H, m), 6.12 (1H, d, J=15 Hz), 6.7–7.7 (11H, m), 7.98 (1H, m), 10.7 (1H, m)
MASS (m/e): 449 (M+), 213 (base)
Elemental analysis: C$_{26}$H$_{28}$ClN$_3$O$_2$·1.5H$_2$O
Calcd.: C 65.47, H 6.55, N 8.81
Found: C 65.88, H 6.44, N 8.78

(10) 1-[2-{5-(3,5-Dichloro-4-hydroxyphenyl)-(2E,4E)-2,4-pentadienoylamino}ethyl]-4-(3-indolyl)piperidine mp: 165°–175° C. (recrystallized from N,N-dimethylformamide)

NMR (DMSO-d$_6$, δ): 1.5–3.6 (13H, m), 5.3 (1H, m), 6.08 (1H, d, J=15 Hz), 6.6–7.6 (10H, m), 8.09 (1H, m), 10.75 (1H, s)

MASS (m/e): 485 (M+2), 483 (M$^+$), 213 (base)

(11) 1-[2-{5-(2-Hydroxy-3-methoxyphenyl)-(2E,4E)-2,4-pentadienoylamino}ethyl]-4-(3-indolyl)piperidine mp: 184°–186° C. (recrystallized from ethanol)

IR (Nujol): 3400, 3240, 1650, 1605, 1600, 1530, 1090, 1005 cm$^{-1}$

NMR (DMSO-d$_6$, δ): 1.4–3.6 (13H, m), 3.78 (3H, s), 6.11 (1H, d, J=15 Hz), 6.6–7.65 (11H, m), 7.90 (1H, t like), 8.95 (1H, br), 10.75 (1H, s)

MASS (m/e): 445 (M$^+$), 226, 213 (base)

(12) 1-[2-{5-(3-Hydroxy-4-methoxyphenyl)-(2E,4E)-2,4-pentadienoylamino}ethyl]-4-(3-indolyl)piperidine mp: 135°–140° C. (recrystallized from ethanol)

IR (Nujol): 3350, 1650, 1615, 1590 cm$^{-1}$

NMR (DMSO-d$_6$, δ): 1.4–3.5 (13H, m), 3.75 (3H, s), 6.11 (1H, d, J=15 Hz), 6.6–7.7 (11H, m), 7.91 (1H, t like), 9.0 (1H, br), 10.7 (1H, s)

MASS (m/e): 445 (M$^+$), 213 (base)

EXAMPLE 8

To a mixture of 1-[2-{5-(4-hydroxy-3-methoxyphenyl)-(2E,4E)-2,4-pentadienoylamino}ethyl]-4-(3-indolyl)piperidine (0.89 g), dry N-methylmorpholine (1.0 g) and dry N,N-dimethylformamide (10 ml) was added slowly acetyl chloride (0.26 g) at 5° to 10° C. After stirring for 1 hours, the reaction mixture was poured into water (50 ml) and stirred for 1 hour. The resulting precipitate was collected, washed with water and then recrystallized from a mixture of ethanol and water (7:3 V/V) to give 1-[2-{5-(4-acetoxy-3-methoxyphenyl)-(2E,4E)-2,4-pentadienoylamino}ethyl]-4-(3-indolyl)piperidine (0.22 g).

mp: 101°–105° C. (recrystallized from ethanol-water (8:2, V/V))

IR (Nujol): 3440, 3250, 1760, 1655, 1620, 1560, 1505 cm$^{-1}$

NMR (DMSO-d$_6$, δ): 1.5–2.4 (6H, m), 2.24 (3H, s), 2.6–3.5 (7H, m), 3.81 (3H, s), 6.20 (1H, d, J=15 Hz), 6.8–7.7 (11H, m), 8.04 (1H, m), 10.73 (1H, s)

MASS (m/e): 487 (M$^+$), 213 (base)

Elemental analysis: $C_{29}H_{33}N_3O_4 \cdot H_2O$
Calcd.: C 68.89, H 6.98, N 8.31
Found: C 68.91, H 6.95, N 8.32

EXAMPLE 9

1-[2-{5-(3-Methoxy-4-propionyloxyphenyl)-(2E,4E)-2,4-pentadienoylamino}ethyl]-4-(3-indolyl)piperidine was obtained according to a similar manner to that of Example 8.

mp: 157°–158° C. (recrystallized from ethanol)

IR (Nujol): 3430, 3250, 3060, 1750, 1655, 1620, 1560 cm$^{-1}$

NMR (DMSO-d$_6$, δ): 1.15 (3H, t, J=8 Hz), 1.5–2.4 (6H, m), 2.62 (2H, q, J=8 Hz), 2.4–3.2 (5H, m), 3.33 (2H, m), 3.82 (3H, s), 6.22 (1H, d, J=15 Hz), 6.8–7.7 (11H, m), 8.05 (1H, m), 10.75 (1H, s)

MASS (m/e): 501 (M$^+$), 213 (base)

Elemental analysis: $C_{30}H_{35}N_3O_4 \cdot H_2O$
Calcd.: C 69.34, H 7.18, N 8.09
Found: C 69.14, H 7.09, N 8.06

EXAMPLE 10

To a mixture of 1-[2-{5-(4-hydroxy-3,5-dimethoxyphenyl)-(2E,4E)-2,4-pentadienoylamino}ethyl]-4-(3-indolyl)piperidine (1 g) and pyridine (10 ml) was added slowly acetyl chloride (0.48 ml) at 5° to 10° C. After 1 hour, the reaction mixture was poured into ice-water and extracted with ethyl acetate. The extract was washed with a saturated aqueous solution of sodium chloride and dried over magnesium sulfate. The solvent was distilled off and the residue was subjected to column chromatography on silica gel and eluted with a mixture of chloroform and methanol (10:1 V/V). The fractions containing the object compound were combined and concentrated under reduced pressure. The residue was treated with a mixture of fumaric acid (83 mg) and methanol (8 ml) and concentrated under reduced pressure to give white crystals. The crystals were recrystallized from ethanol to give 1-[2-{5-(4-acetoxy-3,5-dimethoxyphenyl)-(2E,4E)-2,4-pentadienoylamino}ethyl]-4-(3-indolyl)piperidine ½fumarate (0.25 g).

mp: 202°–209° C.

IR (Nujol): 3400, 1750, 1680, 1615, 1595, 1565 cm$^{-1}$

NMR (DMSO-d$_6$, δ): 1.6–2.15 (5H, m), 2.32 (3H, s), 2.2–3.6 (8H, m), 4.82 (6H, s), 6.22 (1H, d, J=14 Hz), 6.64 (1H, s), 6.7–7.7 (10H, m), 8.29 (1H, m), 10.75 (1H, s)

MASS (m/e): 517 (M$^+$), 213 (base)

Elemental analysis: $C_{30}H_{35}N_3O_5 \cdot \frac{1}{2}Fumarate \cdot 3/2H_2O$
Calcd.: C 63.77, H 6.68, N 6.97
Found: C 63.57, H 6.44, N 6.95

EXAMPLE 11

1-[2-{5-(3,5-Dimethoxy-4-propionyloxyphenyl)-(2E,4E)-2,4-pentadienoylamino}ethyl]-4-(3-indolyl)piperidine ½fumarate was obtained according to a similar manner to that of Example 10.

mp: 188°–192° C. (recrystallized from ethanol)

IR (Nujol): 3400, 1745, 1680, 1615, 1595, 1565 cm$^{-1}$

NMR (DMSO-d$_6$, δ): 1.13 (3H, t, J=7 Hz), 1.6–2.2 (3H, m), 2.2–3.7 (12H, m), 3.81 (6H, s), 6.21 (1H, d, J=15 Hz), 6.62 (1H, s), 6.8–7.6 (10H, m), 8.3 (1H, m), 10.78 (1H, s)

MASS (m/e): 531 (M$^+$), 213 (base)

Elemental analysis: $C_{31}H_{37}N_3O_5 \cdot \frac{1}{2}Fumarate \cdot 3/2H_2O$
Calcd.: C 64.27, H 6.86, N 6.81
Found: C 64.17, H 6.78, N 6.78

EXAMPLE 12

To a mixture of 1-[2-{5-(4-hydroxy-3,5-dimethoxyphenyl)-(2E,4E)-2,4-pentadienoylamino}ethyl]-4-(3-indolyl)piperidine (1.19 g), triethylamine (1.74 ml) and dry N,N-dimethylformamide (12 ml) was added slowly a mixture of ethyl chloroformate (0.33 g) and methylene chloride (0.5 ml) at 0° to 5° C. Similar work up gave 1-[2-{5-(4-ethoxycarbonyloxy-3,5-dimethoxyphenyl)-(2E,4E)-2,4-pentadienoylamino}ethyl]-4-(3-indolyl)-piperidine (0.74 g).

mp: 90°–98° C. (recrystallized from ethanol-water (8:2 V/V))

IR (Nujol): 3360, 3300, 1750, 1640, 1590, 1130, 1000, 735 cm$^{-1}$

NMR (DMSO-d$_6$, δ): 1.28 (3H, t, J=8 Hz), 1.5–3.6 (13H, m), 3.81 (6H, s), 4.23 (2H, q, J=8 Hz), 6.21 (1H, d, J=15 Hz), 6.8–7.7 (10H, m), 8.05 (1H, m), 10.71 (1H, s)

MASS (m/e): 547 (M$^+$), 228, 213 (base)

Elemental analysis: $C_{31}H_{37}N_3O_6 \cdot 2.5H_2O$
Calcd.: C 62.82, H 7.14, N 7.09
Found: C 62.74, H 6.93, N 7.05

EXAMPLE 13

The following compounds were obtained according to a similar manner to that of Example 12.

(1) 1-[4-{5-(4-Ethoxycarbonyloxy-3,5-dimethoxyphenyl)-(2E,4E)-2,4-pentadienoylamino}butyl]-4-(3-indolyl)piperidine mp: 90°–98° C. (recrystallized from ethanol-water (8:2 V/V))

IR (Nujol): 3380, 3250, 1750, 1655, 1620, 1595, 1555, 1130, 1050, 1000, 735 cm$^{-1}$ NMR (DMSO-$d_6$, δ): 1.27 (3H, t, J=8 Hz), 1.4–3.7 (17H, m), 3.72 (6H, s), 4.23 (2H, q, J=8 Hz), 6.20 (1H, d, J=15 Hz), 6.8–7.75 (10H, m), 8.10 (1H, m), 10.76 (1H, s)

MASS (m/e): 575 (M+), 531, 503, 285, 233, 213 (base)
Elemental analysis: $C_{33}H_{41}N_3O_6 \cdot 3/2$ethanol
Calcd.: C 67.01, H 7.81, N 6.52
Found: C 66.39, H 7.74, N 6.52

(2) 1-[4-{5-(3,5-Dimethoxy-4-propionyloxyphenyl)-(2E,4E)-2,4-pentadienoylamino}butyl]-4-(3-indolyl)piperidine hydrochloride mp: 215°–220° C. (recrystallized from acetonitrile)

IR (Nujol): 3250, 2650, 2500, 1760, 1650, 1595, 1130, 1010, 850, 750 cm$^{-1}$

NMR (CDCl$_3$, δ): 1.29 (3H, t, J=8 Hz), 2.65 (2H, q, J=8 Hz), 1.5–3.7 (17H, m), 3.80 (6H, s), 6.35 (1H, d, J=15 Hz), 6.6–7.7 (10H, m), 7.9 (1H, m), 9.05 (1H, m), 11.3 (1H, m)

MASS (m/e): 559 (M+), 503, 233, 213 (base)

(3) 1-[2-[5-{3,4-bis(Ethoxycarbonyloxy)phenyl}-(2E,4E)-2,4-pentadienoylamino]ethyl]-4-(3-indolyl)piperidine mp: 135°–137° C. (recrystallized from a mixture of water and ethanol)

IR (Nujol): 3500, 3350, 1775, 1650, 1620, 1000 cm$^{-1}$
NMR (DMSO-$d_6$, δ): 1.30 (6H, t, J=8 Hz), 1.3–3.5 (13H, m), 4.30 (4H, q, J=8 Hz), 6.25 (1H, d, J=15 Hz), 6.6–7.7 (11H, m), 8.08 (1H, m), 10.73 (1H, s)

MASS (m/e): 529 (M+-46), 457, 285 (base), 213

EXAMPLE 14

To a mixture of 1-[2-{5-(4-hydroxy-3,5-dimethoxyphenyl)-(2E,4E)-2,4-pentadienoylamino}ethyl]-4-(3-indolyl)piperidine (2.0 g), triethylamine (2.9 ml) and dry N,N-dimethylformamide (20 ml) was added slowly a solution of acetylchloride (0.5 g) in methylene chloride (1.0 ml) at 0° to 5° C. After 1 hour, the reaction mixture was poured into water (200 ml) and stirred for 1 hour. The resulting precipitate was collected, washed with water and air-dried at ambient temperature. The precipitate was subjected to column chromatography on silica gel (60 g) and eluted with a mixture of chloroform and methanol (20:1 V/V). The fractions containing the object compound were combined and concentrated under reduced pressure. The residue was recrystallized from ethyl acetate to give pale yellow crystals of 1-[2-{5-(4-acetoxy-3,5-dimethoxyphenyl)-(2E,4E)-2,4-pentadienoylamino}ethyl]-4-(3-indolyl)piperidine (1.35 g).

mp: 169°–172° C.

IR (Nujol): 3380, 3320, 1755, 1650, 1620, 1595, 990, 745 cm$^{-1}$

NMR (CDCl$_3$, δ): 1.5–3.6 (13H, m), 2.32 (3H, s), 3.82 (6H, s), 6.0 (1H, d, J=15 Hz), 6.34 (1H, m), 6.7–7.7 (10H, m), 8.32 (1H, m)

MASS (m/e): 517 (M+), 213 (base)
Elemental analysis: $C_{30}H_{35}N_3O_5$
Calcd.: C 69.61, H 6.82, N 8.12
Found: C 69.35, H 6.82, N 8.02

EXAMPLE 15

To a stirred mixture of 5-[3,5-dimethoxy-4-{(2-methoxyethoxy)methoxy}phenyl]-(2E,4E)-2,4-pentadienoic acid (1.35 g) and triethylamine (1.17 ml) in dry N,N-dimethylformamide (8 ml) was added slowly diphenyl phosphinic chloride (0.97 g) at −10° to −15° C. under an inert atmosphere. After being stirred for 1 hour, a solution of 1-(2-aminoethyl)-4-(3-indolyl)piperidine (0.97 g) in dry N,N-dimethylformamide (8 ml) was added slowly to the reaction mixture at the same temperature. After being stirred for 40 minutes at the same temperature, the reaction mixture was poured into ice-water (160 ml) and extracted with ethyl acetate. The extract was washed with a saturated sodium chloride solution and dried over magnesium sulfate. The solvent was evaporated to give syrup of 1-[2-[5-[3,5-dimethoxy-4-{(2-methoxyethoxy)methoxy}phenyl]-(2E,4E)-2,4-pentadienoylamino]ethyl]-4-(3-indolyl)piperidine (1.97 g).

IR (Nujol): 3300, 1650, 1610, 1580, 1125, 990, 960, 845, 745 cm$^{-1}$

What we claim is:
1. A compound of the formula:

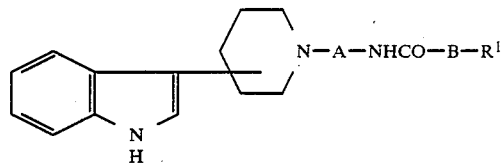

wherein
$R^1$ is aryl substituted with substituent(s) selected from the group consisting of hydroxy, protected hydroxy, halogen and lower alkoxy,
A is lower alkylene, and
B is lower alkenylene,
and a pharmaceutically acceptable salt thereof.

2. A compound of claim 1, wherein
$R^1$ is phenyl substituted with substituent(s) selected from the group consisting of lower alkyl; hydroxy, lower alkoxy(lower)alkoxy(lower)alkoxy, acyloxy, halogen and lower alkoxy.

3. A compound of claim 2, wherein
$R^1$ is phenyl substituted with substituent(s) selected from the group consisting of lower alkyl, hydroxy, lower alkanoyloxy, lower alkoxycarbonyloxy, halogen and lower alkoxy.

4. A compound of claim 3, wherein
$R^1$ is phenyl substituted with mono-, or dihydroxy and mono-, or di(lower)alkoxy.

5. A compound of claim 4, which is 1-[2-{5-(4-hydroxy-3,5-dimethoxyphenyl)-(2E,4E)-2,4-pentadienoylamino}ethyl]-4-(3-indolyl)piperidine.

6. A compound of claim 3, wherein
$R^1$ is phenyl substituted with mono-, or di(lower)-alkanoyloxy and mono-, or di(lower)alkoxy, or with mono-, or di(lower)alkoxycarbonyloxy and mono-, or di(lower)alkoxy.

7. A compound of claim 6, which is 1-[2-{5-(4-acetoxy-3,5-dimethoxyphenyl)-(2E,4E)-2,4-pentadienoylamino}ethyl]-4-(3-indolyl)piperidine.

8. A compound of claim 6, which is 1-[2-{5-(4-ethoxycarbonyloxy-3,5-dimethoxyphenyl)-(2E,4E)-2,4-pentadienoylamino}ethyl]-4-(3-indolyl)piperidine.

9. A pharmaceutical composition comprising a compound of claim 1, as an active ingredient, in association with a pharmaceutically acceptable, substantially non-toxic carrier or excipient.

10. A method for the therapeutic treatment of allergic disease which comprises administering a compound of claim 1 to human beings or animals.

* * * * *